United States Patent
Roger et al.

(10) Patent No.: US 10,194,993 B2
(45) Date of Patent: Feb. 5, 2019

(54) SPINAL SURGERY NAVIGATION

(71) Applicant: Spinal Developments Pty Ltd, A.T.F. The Spinesr Unit Trust, New South Wales (AU)

(72) Inventors: Gregory James Roger, New South Wales (AU); Davor Saravanja, New South Wales (AU)

(73) Assignee: Spinal Developments Pty Ltd, A.T.F The Spinesr Unit Trust, North Sydney, New South Wales (AT)

( * ) Notice: Subject to any disclaimer, the term of this patent is extended or adjusted under 35 U.S.C. 154(b) by 0 days.

(21) Appl. No.: 14/903,732

(22) PCT Filed: Jul. 9, 2014

(86) PCT No.: PCT/AU2014/050117
§ 371 (c)(1),
(2) Date: Jan. 8, 2016

(87) PCT Pub. No.: WO2015/003224
PCT Pub. Date: Jan. 15, 2015

(65) Prior Publication Data
US 2016/0166335 A1 Jun. 16, 2016

(30) Foreign Application Priority Data

Jul. 9, 2013 (AU) .............................. 2013902521

(51) Int. Cl.
*A61F 2/44* (2006.01)
*A61B 34/20* (2016.01)
(Continued)

(52) U.S. Cl.
CPC .......... *A61B 34/20* (2016.02); *A61B 17/1703* (2013.01); *A61B 17/1757* (2013.01);
(Continued)

(58) Field of Classification Search
CPC combination set(s) only.
See application file for complete search history.

(56) References Cited

U.S. PATENT DOCUMENTS

2006/0084889 A1  4/2006  Drumm et al.
2007/0227216 A1  10/2007  Schalliol
(Continued)

FOREIGN PATENT DOCUMENTS

EP  1033113 A1  9/2000
WO  3611624 A2  4/1996
(Continued)

*Primary Examiner* — Sameh Boles
(74) *Attorney, Agent, or Firm* — The Webb Law Firm

(57) ABSTRACT

A system for aiding surgery on a patient is described including a display device and a storage device that stores an image of at least a portion of the anatomy of the patient, including one or more surgical navigation markers positioned on the patient, for display on the display device. An analyzer is adapted to receive positional data of a probe based on positioning of the probe relative to the one or more markers on the patient. Based on the positional data, the analyzer outputs correctional data to adjust an alignment of the image on the display device to match locations of said one or more markers.

22 Claims, 6 Drawing Sheets

(51) Int. Cl.
  *A61B 17/17*  (2006.01)
  *A61B 34/00*  (2016.01)
  *G06F 19/00*  (2018.01)
  *A61B 90/00*  (2016.01)

(52) U.S. Cl.
  CPC ............. *A61B 34/25* (2016.02); *A61B 90/37* (2016.02); *G06F 19/00* (2013.01); *A61B 2034/2055* (2016.02); *A61B 2090/363* (2016.02); *A61B 2090/364* (2016.02); *A61B 2090/367* (2016.02); *A61B 2090/374* (2016.02); *A61B 2090/376* (2016.02); *A61B 2090/3762* (2016.02); *A61B 2090/3916* (2016.02); *A61B 2090/3983* (2016.02)

(56) References Cited

U.S. PATENT DOCUMENTS

| | | | |
|---|---|---|---|
| 2008/0123910 A1* | 5/2008 | Zhu | A61B 90/36 382/128 |
| 2010/0137707 A1* | 6/2010 | Hunter | G06T 3/0068 600/424 |
| 2011/0098722 A1 | 4/2011 | Ulfarsson et al. | |
| 2011/0172674 A1 | 7/2011 | Bankoski et al. | |
| 2013/0012955 A1 | 1/2013 | Lin | |
| 2014/0005524 A1 | 1/2014 | Ulfarsson et al. | |

FOREIGN PATENT DOCUMENTS

| | | |
|---|---|---|
| WO | 2009006935 A1 | 1/2009 |
| WO | 2011134083 A1 | 11/2011 |

* cited by examiner

SPINAL SURGERY NAVIGATION

CROSS-REFERENCE TO RELATED APPLICATIONS

This application is the United States national phase of International Application No. PCT/AU2014/050117 filed Jul. 9, 2014, and claims priority to Australian Patent Application No. 2013902521 filed Jul. 9, 2013, the disclosures of which are hereby incorporated in their entirety by reference.

TECHNICAL FIELD

The present disclosure relates to a system and method used in surgery, such as spinal surgery.

BACKGROUND

Any surgery, such as implant surgery and in particular spinal implant surgery, requires intimate knowledge of the anatomy of the patient, which anatomy can often be quite distorted through degeneration, deformity, neoplasia or trauma. Also required is an ability to navigate safely around that anatomy surgically and an excellent knowledge of the capability and features of the implants designed to help the patient.

While experience can allow a surgeon or surgical team to perform procedures without the assistance of aids, this experience can take some time to accumulate. In less experienced hands, as well as for more complex cases with grossly distorted anatomy, a number of systems have been devised to help make the surgery more reliable and safe. An example of one such system relies on linking infrared navigation systems with pre-operative or intra-operative computed tomography (CT) scans on the patient. Such systems while very helpful can be of limited assistance once surgery has commenced.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

In one aspect, a system for aiding surgery on a patient is disclosed comprising:
 a display device;
 a storage device that stores an image of at least a portion of the anatomy of a patient of interest;
 an analyser that compares the image with the position of one or more surgical navigation markers positioned on the patient and provides an output of said comparison to the display device; and
 an input device that is capable of receiving data from a probe that is positionable relative to said one or more markers and delivering said data to the analyser;
 wherein said analyser processes said data and outputs correctional data that adjusts the alignment of said image on said display device to match with the location of said one or more markers.

In another aspect there is provided a system for aiding surgery on a patient comprising:
 a display device; and
 a storage device that stores an image of at least a portion of the anatomy of the patient, including one or more surgical navigation markers positioned on the patient, for display on the display device,
 an analyser adapted to receive positional data of a probe based on positioning of the probe relative to one or more of said markers on the patient; and
 wherein, based on said positional data, said analyser outputs correctional data to adjust an alignment of the image on said display device to match locations of said one or more markers.

While any one of the systems disclosed herein can be used in a range of surgical applications the system can be used for and has significant application in spinal surgery, particularly surgery for correction of deformities of the spine. The following embodiments are described with reference to spinal surgery although it will be appreciated that the system could be utilised, with modification where necessary, in other surgical situations.

Some of the defined components of the system can be integrated into a single device. It will, however, be appreciated that the components could be provided separately and connected physically and/or electronically as required.

The system is designed to be used in a surgical setting. Some components may be provided, by necessity, in the surgical setting whereas others may be located outside the surgical setting and even remotely.

By providing positional data and correctional data, the system can allow the alignment of the displayed image to be registered or re-registered with the patient during a surgical process. The position of the probe relative to the patient can be continually represented and updated in the displayed image as the probe moves. By re-registering the displayed image, the position of the probe relative to the patient, in the displayed image can more accurately represent the actual positioning of the probe relative to the patient, and therefore surgical navigation using information in the displayed image can be enhanced. The surgical navigation can be more accurate at any given time during surgery, notwithstanding any manipulation of the patient's anatomy that may have occurred. Additionally or alternatively, the probe can be used to identify positions of anatomical landmarks and/or apparatus such as surgical screws and, following accurate registration of the displayed image, positional data from the probe can be used to accurately update or introduce representations of the identified features in the displayed image. These and other optional features and advantages of the system are discussed below.

The display device can comprise any display suitable for the purposes described herein. It can comprise, for example, a television screen, a computer monitor, a LED display, a hologram/holograph, a touch screen or a combination of such displays. The display device can comprise multiple display screens. It can also comprise one screen capable of displaying different images simultaneously or sequentially as required.

The storage device, can comprise any suitable data storage device.

The analyser can comprise a processor and/or other appropriate electronic circuitry so as to be capable of comparing an image with other inputs as defined herein.

Positional data of the probe may be determined at least partially using a navigation device such as a camera, e.g. an infrared (IR) camera, which can monitor changes in position of the probe. The ER camera may provide a form of input device to the analyser.

The image can be provided by a computed tomography (CT) device, a MRI device and/or an X-ray device and/or any other means of generating scaleable images or representations of the anatomy. For simplicity, in subsequent discussions reference is made to use of a CT scanner and to CT images, etc. However, it will be appreciated that other types of scanners or devices and other types of images may be used.

For spinal surgery applications, to position the one or more surgical markers, the surgeon may first expose the bony anatomy of the spine, posteriorly, laterally or anteriorly, at the desired levels. A first navigation marker may then be firmly clamped or otherwise mounted to a piece of bone away from the area to be resected or operated thereon, usually the next vertebra up or down the spine, and usually on the spinous process in a posterior approach.

One or more of the surgical markers, such as the first marker, and/or the probe, can comprise or support one or more reflective components, such as reflective balls. The reflective components can be designed to reflect light, of a particular frequency, for example infrared (IR), with a navigation device, such as an IR camera, having a capability to remotely detect the position of the markers and/or probe being then part of the system. Other surgical instrumentation may also comprise or support similar reflective components for the purposes of position detection using the navigation device such as the IR camera. For example, the imaging device used to provide the image, e.g. a fixed or mobile CT scanner, or a surgical drill, can comprise or support reflective components. In use, the IR camera is pointed at the whole operative site, including the surgical marker(s) clamped or otherwise mounted to bone.

In addition to or as an alternative to markers comprising reflective components such as balls, other markers such as fiduciary screws can be secured to bony parts. The screws used for this purpose can be craniofacial screws, for example, screws with about a 2 mm diameter and an 8 mm or 6 mm length. Such screws can be relatively easy to imbed in the bone and do not obstruct subsequent surgery. These screws, which will show up in an intra-operative imaging scan, can be used, e.g., exclusively, for a checking purpose described hereunder. Other suitable types and dimensions of screws can be envisaged.

Once the patient has been prepared as described above, the image, e.g. a CT scan, can then be taken. This can be achieved through use, for example, of a mobile CT scanner that is brought into the operating theatre. In taking the CT scan, the aim may be to show all of the desired operative levels as well as the markers, e.g. the fiduciary screws. Two or more CT scans may therefore be taken at different anatomical levels. The CT scans may be combined, e.g., "stitched together", to create a three dimensional image. The fiduciary screws may be used as orientation points to ensure that the combined CT scans are appropriately aligned. By creating a three dimensional image in this manner, a surgeon or other practitioner may advance or scroll through different levels in the image as surgery proceeds along the spine or otherwise. The displayed image may therefore provide navigational information to the surgeon at different levels of the anatomy that is subject to the surgical procedure.

The CT scanner can be connected to and/or monitored by the IR camera and the subsequent images can then be looked at in all three planes simultaneously on three separate regions or windows of a relatively large output screen comprising the display device. Through the connection/monitoring, the system can determine the positioning of the CT scanner relative to the patient at the time of obtaining the images. The images typically show the patient as they are lying on the operating table at the time the CT scan is taken and the fiduciary screws can be seen in the bone. Furthermore, the navigating probe, having one or more reflective markers, as described herein, can then be used by the surgeon such that it effectively points at various parts of the anatomy. Given the nature of the navigating probe, its location relative to the patient can be readily superimposed over the CT images of the patient's anatomy.

In the case of spinal surgery, the system can be used to identify the correct placement point for one or more pedicle screws, (and optionally also other surgical hardware or fixation devices) as well as the correct angle to drill for them. The pedicle screws may be adapted to support a spinal rod or otherwise. As the pedicles of the vertebra are drilled, the navigation probe can also be inserted into the drill hole to check its location and orientation. The planned screw size can also be superimposed, rather than just the line of the probe, to ensure the screw diameter does not exceed the available space.

During this procedure, the markers such as the fiduciary screws can be used, from time to time, to check the accuracy of the navigation. Because the fiduciary screws are in situ when the CT scan is taken, they show on the scans. The navigation probe as superimposed on the displayed image should then be shown exactly on the scanned screws when the probe is touched onto the actual screws by the surgeon. However, this is often not the case, with the screws appearing to be 1 or more millimeters away from the position of the probe when viewed on the display device, despite the fact the probe is placed exactly on the screws, e.g. exactly in the screw head, or as exactly as the head design allows. This "offset" could require the surgeon to estimate a correction for the image shown for the other areas of anatomic interest, such as the pedicle of the vertebra.

There are many causes for this apparent "offset". A first navigation marker (e.g. a marker comprising reflective componentry) may shift slightly due to softness of the bone that it is mounted on and/or by virtue of being knocked by a surgical instrument or one of the surgical team. Further, as the spine is realigned through surgical instrumentation or positioning of a movable operating table, the relative position of each vertebra to the vertebra on which the navigation maker is mounted may shift. Likewise, image acquisition and hence navigation can be compromised by changing surgical retraction during a procedure, either during or after image acquisition. These are just three examples of the many was in which the apparent position of a point, such as a fiducial screw, no longer matches its position on the CT image of the navigation system.

The system as described herein provides the surgeon or surgical team with a means of correcting for such offsets when they occur.

In one embodiment, correction can be achieved through positioning one or more fiduciary screws to the patient. It will be appreciated that other suitable markers could be used in place of fiduciary screws. In one embodiment, at least three fiduciary screws can be positioned on the patient, e.g. on each individual vertebra, and each aligned with a different anatomical axis/plane to that of the others. The use of at least three fiduciary screws can ensure that the CT image can be realigned in all three axes/planes, so ensuring an appropriate three dimensional image of the anatomy of the patient. However, in general, alignment of the image to match with the location of one or more markers, such as fiduciary screws, may be along any one or more axes.

In one embodiment, the analyser of the system can make an initial determination of the position of the three fiduciary screws and so form a three dimensional image. For example, the analyser can in effect create a three dimensional solid based on the initial determination of the three fiduciary screws. The surgeon can then use the navigation probe to physically touch the actual fiduciary screws to generate positional data. The analyser can then use the positional data provided by this action to output correctional data and form a corrected three dimensional solid and then align the CT image on the screen to the actual location of the body.

In a further embodiment, a fourth or greater numbers of fiduciary screws can be used to provide additional positional data to the analyser so providing improved accuracy. The output correctional data from the analyser and imagery generated can be stored by the system and can be retrievable so allowing the surgeon to revert to any earlier image should that be required.

In this embodiment, the analyser can be controlled by software and rely on an algorithm to compare the three dimensional solids and then adjust the alignment of the three dimensional image.

The software may be adapted to perform feature detection on the stored image. For example, the software may include an edge detection module, which is adapted to determine the edges of bones in the image to further assist in analysis and representation of the anatomy of the patient.

In addition to or instead of the above process for achieving correctional alignment of the displayed image, the navigation marker can comprise relatively fine adjustment devices, such as vernier drives, that allow the reference frame or marker to be rotated and/or translated in up to all three axes/planes as necessary. In this embodiment, the surgeon can touch the navigation probe to each of the at least three fiduciary screws, hereinafter referred to "probed", and then operate the adjustment devices each time as appropriate to ensure the image is brought into alignment. In one embodiment, the analyser can provide an output to the surgeon indicative of which adjustment is necessary. The output may be a corrected alignment sketch superimposed on the displayed image, for example. As each fiduciary screw is probed, the analyser can provide an output of which adjustment is required to change the image with reference to the real position without changing the recently corrected image based on the previous probed fiduciary screw. When the third fiduciary screw is probed, there should only be one plane of correction. However, it will be appreciated that this might not align exactly with the plane of the navigation guide's correctional verniers and so two planes may need to be tweaked.

In yet another embodiment, the probe can be used in conjunction with other features. For example, following alignment of the image, one or more pedicle screws can be inserted into the spine. The image can then be updated using positional data generated by the navigating probe touching a pedicle screw e.g., the driving head of a pedicle screw. Through knowledge of the length (and other dimensions) of the screw, a three dimensional image of the screw can be added to the on-screen navigation image based on the positional data. Additionally or alternatively, reflective componentry (e.g. a navigation array) may be connected to the driving head of the pedicle screw to enable a determination to be made of pedicle screw location and enable addition of the screw to the image.

In a further embodiment, the one or more pedicle screws can each comprise a shank and drive system and a head portion. The head can be polyaxially connected to the screw shank and so may bear a variable relationship to the position of the screw shank itself. During insertion of the screw, this polyaxial feature is disabled (the screw head is held by the driver aligned with the shank) and so the final driven position of the screw can be determined before disconnection of the driver and the CT image updated with this screw position. In this way the pedicle screw can then be used as a fiduciary screw for the rest of the procedure. This will allow subsequent correction of anatomical alignment, of the vertebra to be checked as the screws move with the anatomy at each vertebra. In this embodiment, the new screw position can then be shown on screen along with the old screw position to allow visualization of the corrected lordosis or scoliosis without the need for further imaging. While the bony anatomy can be updated with further scans, the screw position in the hone remains fixed and allows inferring of the bony position.

In a still further embodiment, the system can run software that allows a lordosis correction, kyphosis correction, scoliosis correction, or listhesis correction to be sketched or otherwise superimposed onto the three dimensional image on the display device. This in turn provides an indication of what movement of the pedicle screws is required. In this embodiment, after the pedicle screws are moved, they can be compared to the desired, corrected positions as superimposed on the displayed image. The approach provides a surgeon feedback as to the compliance of the surgery with pre-operatively planned correction. This ability to plan, monitor and finally confirm the degree of correction can rely on use of a three dimensional representative figure, such as a stick figure, superimposed on the displayed image so that it is in view no matter where the image is scrolled to within the CT scan.

The system can run software that identifies features of bony anatomy of the patient including the spinous processes, lamina, pars interarticularis, articular processes, and/or the transverse processes. The system may allow a point to point line to be assembled on the display device. The provision of a means of point to point line assembly also allows the surgeon to, if desired, pick out key features, say the tips of the spinous processes or the individual pedicle screws, and link them with a line. A similar process can occur for the Transverse Processes and so on. Once the point to point line has been superimposed, the required angular correction over that line could be entered into the system, for example as an angle or vector.

The software that is part of the system can be used to prevent undesired movement of the spine or other anatomy during surgery. For example, in relatively complex scoliosis cases, the anterior spinal artery can be threatened by excessive traction during straightening of the spine. As the anatomic position of the anterior spinal artery is along the posterior vertebral bodies, the point to point line (which may be a thick line as the artery branches and wanders) may be superimposed over the image and treated as an "axis" so that it can be checked, for example, that no or relatively small overall lengthening of the artery occurs while the vertebra are rotated with respect to each other.

Each marker/screw may comprise a reference point that is probed. The reference point may be a head of a screw or otherwise. In one embodiment, a connector can be provided that allows the navigation probe to be clicked into a reference point. The reference point may be part of the connector. The connector may be provided as part of the probe, the navigation marker and/or one, some or all of the fiduciary screws. The connector is provided such that relatively quick and accurate sampling of the location of these features can be achieved. The connector may be integral with marker/ screw and may take the form of a cap that is positioned at the head of the marker/screw. The cap may be a locking cap that locks a spinal rod in place relative to the screw. The locking cap may be permanent or temporary. For example, when the locking cap is temporary, the locking cap may be used only for the purposes of surgical navigation and may be removed and optionally replaced with a different locking cap at completion of surgery. Each of the fiduciary screws can be designed such that the tip of the navigation probe engages with the head of the screws, or connector/locking cap, at an exactly known location. This location can be readily identifiable on the CT image and can be provided with a relatively soft attachment. In use, the navigation probe can be held so that the surgeon does not need to maintain attention to the probe being in the right spot while looking at the screen, and yet release relatively easily.

In yet another embodiment, particularly for minimally invasive surgery (MIS), the pedicle screws may be inserted through tubes that are placed in relatively small stab incisions in the patient's body. When a tube is used, a connecter may optionally be provided that attaches to the pedicle screw and which comprises an extension piece that extends from the pedicle screw, through the tube, up to or beyond the distal end of the tube. The navigation probe may contact and/or click (e.g. snap-fit) into the extension piece via the distal end of the tube, and the extension piece may therefore act as another reference point for the surgical navigation. Additionally or alternatively, the tube itself may provide a reference point for the surgical navigation.

In yet a further embodiment, the system can be used in a determination of what degree of bending of a rod designed to extend between the vertebrae is required. It can also be used to guide rod length selection and the degree of correction needed to be placed in the rod bending. In this embodiment, a representative figure line connecting the pedicle screw heads can show how the rod needs to be bent for an exact/desired fit as well as the overall length required. Additionally or alternatively, the system can be used to adjust the positioning of the pedicle screws to at least partially align with the rod shape.

The system can then add in the angular correction data needed for a correct rod bend. Once the angular correction data has been added, the system may provide the degree of bending and the angular correction data as an output to a spinal rod bending device that bends the rod to the degree necessary to achieve a desired surgical outcome.

When the rod is in place, the positioning of the pedicle screws may be checked and/or updated on the displayed image, e.g. by touching the drive head with the probe, thus providing a form of re-registering of the pedicle screw positions with the displayed image. In general, the positions of any markers/screws may be registered or re-registered throughout the surgical procedure, without the need for further scanning.

Following from discussions above, in one aspect of the present disclosure, there is disclosed a spinal rod bending system comprising:
  a rod bender;
  a control system that receives an input from a system as defined herein and controls the rod bender to produce a rod having the required rod bending in the required location.

In yet another aspect, there is disclosed a method of aligning an image of at least a portion of the anatomy of a patient with one or more navigation markers positioned on the anatomy comprising:

imaging the anatomy to allow determination of an imaged position of the marker(s);

bringing a navigation probe to a position relative each of the marker(s) to determine the actual position of the marker(s);

determining the misalignment between the imaged position of the marker(s) and the actual position of the marker(s); and adjusting the imaged position of the markers(s) to align with their actual position.

In another aspect there is provided an apparatus comprising:
  the system of the preceding aspect; and
  a spinal rod bending device comprising:
  a rod bender; and
  a controller that receives an input from the system and controls the rod bender to produce a rod having a required degree of bending for a required location of the patient.

In this aspect, the navigation probe can be brought into contact with each of the marker(s).

In this aspect, additional markers, such as fiduciary screws, can be positioned on the anatomy and be probed by the navigation probe.

In this aspect, the method can be performed using the system as defined herein.

The systems and methods of the present disclosure can potentially be more accurate and user friendly than hitherto known systems and methods while furthermore increasing the level of useful information available to the surgeon or surgical team. The ability to intra-operatively determine key features of the anatomy of a patient, for example spinal kinematics, to image them correctly relative to their actual positions, and then respond quickly and appropriately, minimizes potential operative time and also the need to re-scan the patient. As each intra-operative CT is approximately equivalent to 300 chest X-Rays, such a reduction is of significant benefit.

BRIEF DESCRIPTION OF DRAWINGS

By way of example only, embodiments are now described with reference to the accompanying drawings, in which.

DESCRIPTION OF EMBODIMENTS

Figure 1:
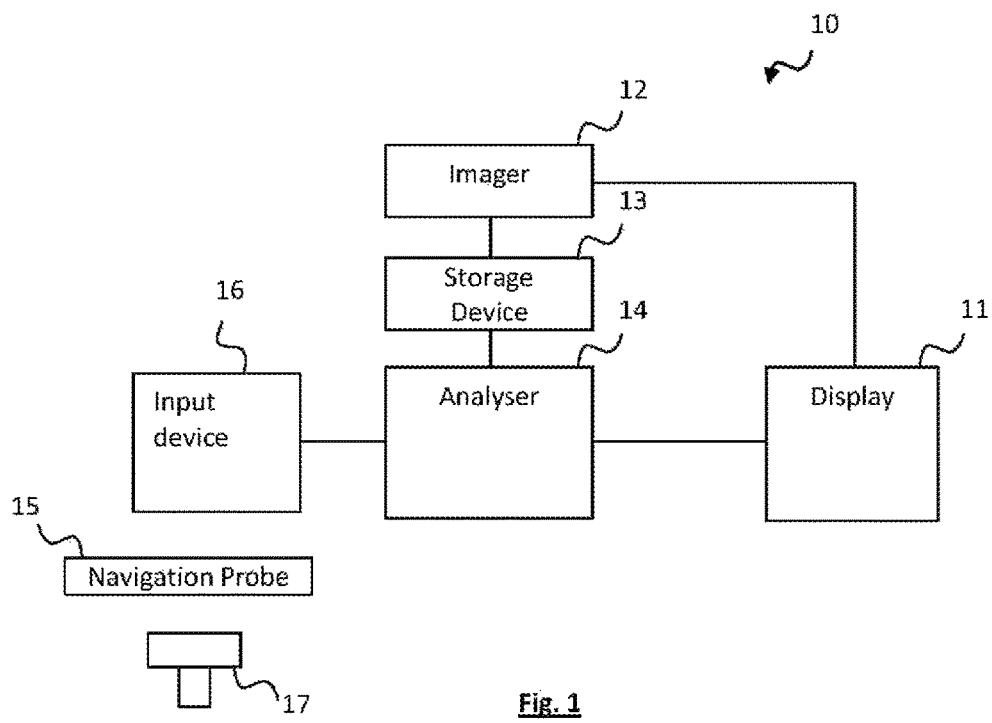
FIG. 1 is a schematic depiction of an embodiment of the system as described herein.

One embodiment of the surgical system as described herein is depicted generally as 10 in FIG. 1. The depicted system 10 is designed to aid a surgeon or surgical team performing corrective spinal surgery. The system 10 comprises a computer monitor 11 that serves to display CT images taken of a patient's spine by a CT imager 12. The images displayed on display 11 are stored in a suitable data storage device 13.

The system further comprises an analyser 14 in the form of a computer processor. The analyser 14 is designed to compare the CT image provided by the imager 12 with the position of one or more surgical navigation markers 17 positioned on the patient. The position of the one or more markers 17 is determined through use by the surgeon of a surgical navigation probe 15 that can be moved and brought into contact with the one or more markers 17. The positional data from the probe 15 is provided through an input device 16 to the analyser 14 which in turn provides an output of said comparison to the display device 11. The use of the probe allows the analyser 14 to generate correctional data so allowing for correctional alignment of the displayed CT image to match with the actual position of the one or more markers 17 on the patient.

Figure 2:
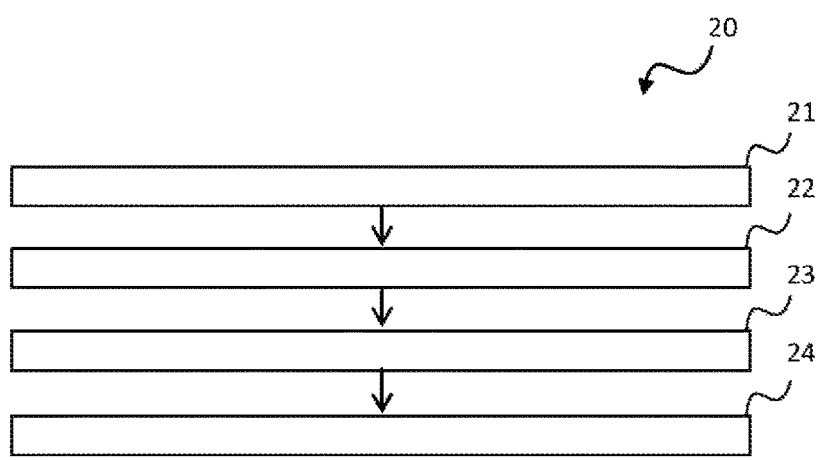
FIG. 2 is a flowchart of one embodiment of the use of the system as described herein.

One embodiment of a method of aligning a CT image of at least a portion of the anatomy of a patient with one or more navigation markers positioned on the anatomy is depicted generally as 20 in FIG. 2. The method 20 comprises:

a step 21 of imaging the anatomy to allow determination of an imaged position of the marker(s);

a step 22 of touching each of the marker(s) with a navigation probe to determine the actual position of the marker(s); and a step 23 of determining the misalignment between the imaged position of the markers) and the actual position of the marker(s); and a step 24 of adjusting the imaged position of the markers(s) to align with their actual position.

In this method, surgical markers, such as fiduciary screws, can be positioned on the anatomy and probed by the navigation probe. The method 20 can be performed by the system 10 depicted in FIG. 1.

It will be appreciated that many of the components of the system depicted in FIG. 1 can be integrated into a single device. It will, however, be appreciated that the components could be provided separately and connected physically and/or electronically/electromagnetically as required.

The system 10 is designed to be used in a surgical setting. Some components may be provided, by necessity, in the surgical setting whereas others may be located outside the surgical setting and even remotely.

The display 11 can comprise any display suitable for the purposes described herein. It can comprise a television screen, a computer monitor, a LED display, a touch screen, a hologram/holograph, or a combination of such displays. The display can comprise multiple display screens. It can also comprise one screen capable of displaying different images simultaneously or sequentially as required.

The storage device 13 can comprise any suitable data storage device.

The analyser 14 can comprise a processor and/or other appropriate electronic circuitry so as to be capable of comparing an image with other inputs as defined herein.

The input device 16 can comprise a navigation device such as a camera, e.g. an infrared (IR) camera, which can monitor changes in position of the probe and other hardware.

The imager 12 can comprise a computed tomography (CT) device, an MRI device and/or an X-ray device and/or any other means of generating scaleable images or representations of the anatomy. For simplicity, subsequent discussions refer to use of a CT scanner and CT images. However, it will be appreciated that other types of scanners or devices and other types of images can be used.

Figure 3:
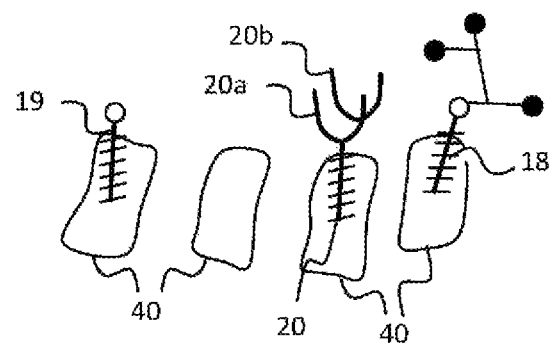
FIG. 3 is an illustrative representation of the spine and screws.

To position the one or more surgical markers, the surgeon first exposes bony anatomy of the spine 40, posteriorly, laterally, obliquely, or anteriorly, at the desired levels. FIG. 3 provides an illustrative depiction of this. A first navigation marker 18 can then be firmly clamped or otherwise mounted to a piece of bone away from the area to be resected or operated thereon, usually the next vertebra up or down the spine 40 and usually on the spinous process in a posterior approach.

The surgical marker 18 and probe can comprise or support one or more reflective components, such as reflective balls. Additionally, the imager 12 or other surgical instruments such as drills can comprise or support one or more reflective components, such as reflective balls. The reflective components can be designed to reflect light of a particular frequency, for example infrared (IR), with a navigation device, such as the IR camera, having a capability to remotely detect the position of the markers, probe and other instruments being then part of the system. In use, the IR camera is pointed at the whole operative site, including the surgical marker(s) clamped or mounted to bone.

The position of the first marker 18 may be determined using the reflective components and/or through being probed, and initial registration of the displayed image may therefore be made using the first marker.

In addition, other markers, described herein as fiduciary screws 19 can be secured to other bony parts. The screws used for this purpose can be craniofacial screws, for example, screws with about a 2 mm diameter and a 6 mm length. Such screws can be relatively easy to imbed in the bone and do not obstruct subsequent surgery. These screws, which will show up in an intra-operative imaging scan, can be used for a checking purpose described hereunder. Other suitable types and dimensions of screws can be envisaged.

Once the patient has been prepared as described above, a CT scan can then be taken (step 21 of FIG. 2). This can be achieved through use of a mobile CT scanner that is brought into the operating theatre. In taking the CT scan, the aim is to show all of the desired operative levels as well as the fiduciary screws.

The CT scanner can be connected or viewed by the IR camera and subsequent CT images obtained in all three planes can be looked at simultaneously on three separate regions or windows of the display 11. These images typically show the patient as they are lying on the operating table and the fiduciary screws 19 can be seen in the bone. Furthermore, the navigation probe 15, having one or more reflective markers as described herein can then be used by the surgeon such that it effectively points at various parts of the anatomy. Given the nature of the navigation probe 15, through monitoring using the IR camera, its location relative to the patient can be readily superimposed over the CT images of the patient's anatomy.

Figure 7:
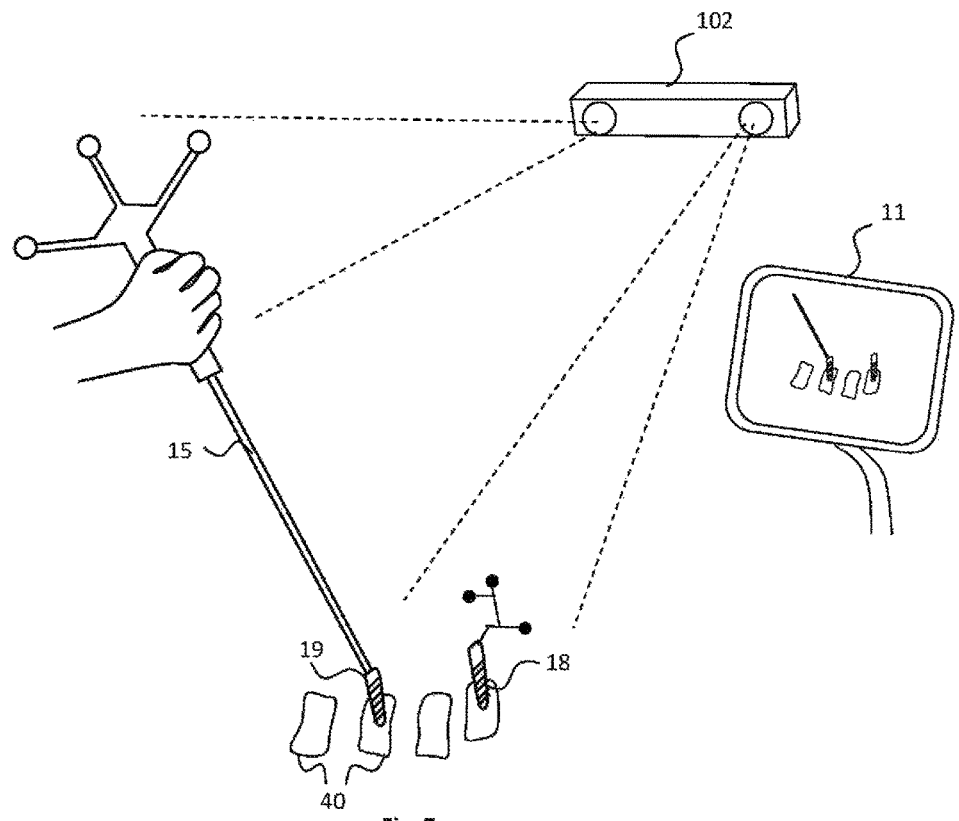
FIG. 7 is an illustration of an embodiment of the system as described herein.

An illustration of a surgeon manipulating the probe 15, in order to probe the position of a fiduciary screw 19 located in the spine 40 of a patient's body, in the field of view of an IR camera 102, is provided in FIG. 7. Another surgical marker 18 is also located on the spine.

In the case of spinal surgery, the system 10 can be used to identify the correct placement point for one or more pedicle screws 20, as well as the correct angle, and depth, to drill for them. As the pedicles of the vertebra are drilled, the navigation probe 15 can also be inserted into the drill hole to check its location and orientation. The planned screw size can also be superimposed, rather than just the line of the probe, to ensure the screw diameter and length do not exceed the available space.

During this procedure, the fiduciary screws 19 can be used, from time to time, to check the accuracy of the navigation. Because the fiduciary screws are in situ when the CT scan is taken, they show on the CT images. The navigation probe 15 as superimposed on the displayed images should then be shown touching exactly onto the heads of the scanned screws 19 when the probe 15 is touched onto the heads of the actual screws by the surgeon. However, this is often not the case with the screws appearing to be 1 or more millimeters away from the position of the probe when viewed on the display, despite the fact the probe is placed exactly in the screw head, or as exactly as the head design allows. This "offset" could require the surgeon to estimate a correction for the image shown for the other areas of anatomic interest, such as the pedicle of the vertebra.

The system as described herein provides the surgeon or surgical team with a means of correcting for such offsets when they occur.

Additional correctional data can be achieved through positioning additional fiduciary screws 19 to the patient. It will be appreciated that other suitable markers could be used. In this embodiment, at least three fiduciary screws can be positioned to the patient, each on a different plane to that of the others. The use of at least three fiduciary screws can ensure that the CT image can be realigned in at least three axes/planes, so ensuring an appropriate three dimensional image of the anatomy of the patient. At least three fiduciary screws may be positioned on each segment (e.g., on each vertebra). As the spine consists of multiple intercalated segments with intrinsic abilities for movement in any plane at any time point, the use of three fiduciary markers per segment may allow ultimate control of subsequent image manipulation and hence navigation.

In one embodiment, the analyser 14 of the system 10 can make an initial determination of the position of the three fiduciary screws and so form a three dimensional image. For example, the analyser can in effect create a three dimensional solid based on the initial determination of the three fiduciary screws. The surgeon can then use the navigation probe 15 to physically touch the actual fiduciary screws 19 to generate positional data. The analyser 14 can then use the positional data provided by this action to form a corrected three dimensional solid and then manipulate or align the CT image on the display to the actual location of the body, thus providing a form of registration or re-registration of the image and the patient's body.

In a further embodiment, a fourth or greater number of fiduciary screws 19 can be used to provide additional correctional data to the analyser 14 so providing improved accuracy. The correctional data from the analyser 14 and imagery generated can be stored in the storage device 13 of the system 10 and can be retrievable so allowing the surgeon to revert to any earlier image should that be required.

In this embodiment, the analyser 14 can be controlled by software and rely on an algorithm to compare the three dimensional solids and then adjust the alignment of the image.

Generally, in embodiments of the present disclosure it will be recognised that components of the system, such as the analyser, storage device and/or input device may form part of and/or be controlled by a processor. The processor may comprise number of control or processing modules for controlling one or more components of the system and may also include one or more storage elements, for storing data such as images. The modules and storage elements can be implemented using one or more processing devices and one or more data storage units, which modules and/or storage devices may be at one location (e.g., in a surgical control station) or distributed across multiple locations and interconnected by one or more communication links.

The modules can be implemented by a computer program or program code comprising program instructions. The computer program instructions can include source code, object code, machine code or any other stored data that is operable to cause the processor to perform the steps described. The computer program can be written in any form of programming language, including compiled or interpreted languages and can be deployed in any form, including as a stand-alone program or as a module, component, subroutine or other unit suitable for use in a computing environment. The data storage device(s) may include suitable computer readable media such as volatile (e.g. RAM) and/or non-volatile (e.g. ROM, disk) memory or otherwise.

In addition to or instead of the above process for achieving correctional alignment of the displayed image, the one or more of the navigation markers can comprise relatively fine adjustment devices, such as vernier drives, that allow the marker to be rotated and/or translated in up to all three axes/planes as necessary. In this embodiment, the surgeon can touch the navigation probe 15 to each of the at least three fiduciary screws 19, hereinafter referred to "probed", and then operate the adjustment devices each time as appropriate to ensure the image is brought into alignment. In one embodiment, the analyser 14 can provide an output to the surgeon indicative of which adjustment is necessary. As each fiduciary screw 19 is probed, the analyser 14 can provide an output of which adjustment is required to change the image with reference to the real position without changing the recently corrected image based on the previous probed fiduciary screw 19. When the third fiduciary screw 19 is probed, there should only be one plane of correction. However, it will be appreciated that this might not align exactly with the plane of the navigation guide's correctional verniers and so two planes may need to be tweaked.

In yet another embodiment, the probe 15 can be used in conjunction with other features. For example, following alignment of the image, one or more pedicle screws 20 can be inserted into the spine. The image can then be updated using the driving head of the pedicle screw 20 and the known length (and of course all other dimensions) of the screw to enable a three dimensional image of the screw to be added to the on-screen navigation image.

In a further embodiment, each pedicle screw 20 can comprise a shank and drive system and a head portion. The head can be polyaxially connected to the screw shank and so may hear a variable relationship to the position of the screw shank itself.

During insertion of the screw 20, this polyaxial feature is disabled (the screw head is held by the driver aligned with the shank) and so the final driven position of the screw can be determined before disconnection of the driver and the CT image updated with this position. In this way the pedicle screw 20 can then be used as a fiduciary screw 19 for the rest of the procedure. This will allow subsequent correction of anatomical alignment of the vertebra to be checked as the screws will have moved with the anatomy. In this embodiment, the new screw position 20*b* (see FIG. 3) can then be shown on screen along with the old screw position 20*a* to allow visualization of the corrected lordosis or scoliosis without the need for further imaging. While the bony anatomy can be updated with further scans, the screw position in the bone remains fixed and allows inferring of the bony position.

Figure 4:
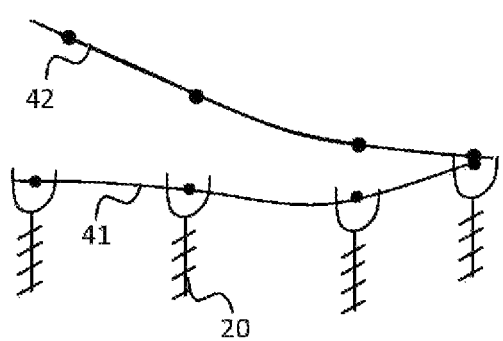
FIG. 4 is an illustrative representation of a spine and how its alignment can be changed.

In a still further embodiment, the system can run software that allows a lordosis, scoliosis or listhesis correction to be sketched or otherwise superimposed onto the three dimensional image on the screen of the display 11 (see FIG. 4). This in turn provides an indication of what movement of the pedicle screws is required. After the pedicle screws are moved, they can be compared to the desired, corrected positions as superimposed on the displayed image. The approach provides a surgeon feedback as to the compliance of the surgery with pre-operatively planned correction. This ability to plan, monitor and finally confirm the degree of correction can rely on use of a three dimensional representative figure, such as a stick figure, superimposed on the displayed image so that it is in view no matter where the image is scrolled to within the CT scan. A point to point line 41 may be assembled. The provision of a means of point to point line assembly also allows the surgeon to, if desired, pick out key features, say the tips of the spinous processes or the pedicle screws, and link them with the line 41. A similar process can occur for the Transverse Processes and so on. Once the point to point line 41 has been assembled, the required angular correction 42 over that line 41 could be entered into the system, for example as an angle or vector.

The software that is part of the system 10 can be used to prevent undesired movement of the spine or other anatomy during surgery. For example, in relatively complex scoliosis cases, the anterior spinal artery can be threatened by excessive traction during straightening of the spine. As the anatomic position of the anterior spinal artery is along the posterior vertebral bodies, a point to point line (which may be a thick line as the artery branches and wanders) may be superimposed over the image and treated as an "axis" so that, for example, no or relatively small overall lengthening of the artery occurs while the vertebra are rotated with respect to each other.

Each marker/screw can comprise a reference point that is probed. The reference point may be a head of a screw or otherwise. A connector can be provided that allows the navigation probe 15 to be clicked into each reference point can be provided as part of the probe 15, the navigation marker 18 and/or one, some or all of the fiduciary screws 19. The connector is provided such that relatively quick and accurate sampling of the location of these features can be achieved. Each of the fiduciary screws 19 can be designed such that the tip of the navigation probe engages with the head of the screws at an exactly known geometric location. This location can be readily identifiable on the CT image and can be provided with a relatively soft attachment. In use, the navigation probe 15 can be held so that the surgeon does not need to maintain attention to the probe 15 being in the right spot while looking at the screen of the display 11, and yet release relatively easily.

The system can be used in a determination of what degree of bending of a rod designed to extend between the vertebrae is required. It can also be used to guide rod length selection and the degree of correction needed to be placed in the rod bending. In this embodiment, a representative figure line connecting the pedicle screw 20 heads can show how the rod needs to be bent for an exact/desired fit as well as the overall length required.

Figure 5:
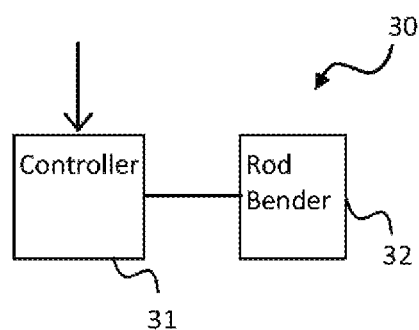
FIG. 5 is a schematic depiction of a rod bender apparatus as described herein.

The system can then add in the angular correctional data needed for a correct rod bend. Once the angular correctional data has been added, and as depicted in FIG. 5, the system 10 can provide the degree of bending and the angular correction data to an apparatus 30 comprising a controller 31 and a rod bending device 32 that bends the rod to the degree necessary to achieve a desired surgical outcome.

Figure 6:
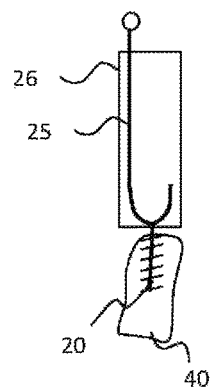
FIG. 6 is an illustrative representation of a screw having an extension portion.

Referring to FIG. 6, in a further embodiment employed in minimally invasive surgery (MIS), a pedicle screw 20 is implanted via a tube 26 that is placed in relatively small stab incisions in the patient's body. A connecter 25 is provided that attaches to the pedicle screw 20 and which comprises an extension piece that extends from the pedicle screw, through the tube 26, and beyond the distal end of the tube 26. The navigation probe can contact and/or snap-fit into the extension piece of the connector 25 in order to probe the positioning of the pedicle screw 20.

Figure 8:
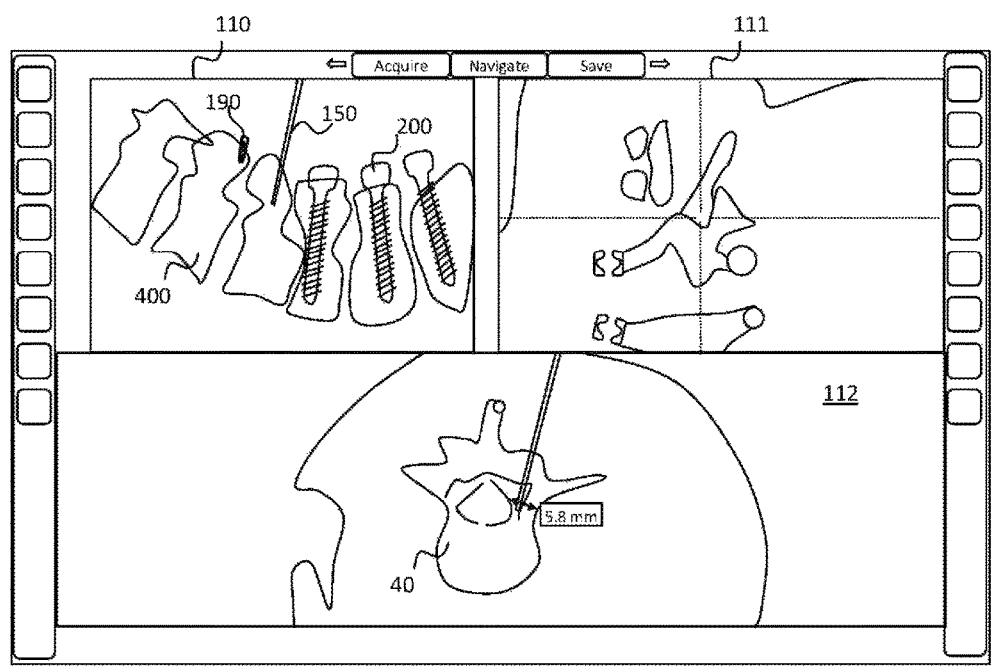
FIGS. 8 to 10 illustrate example outputs of a display according to embodiments of the system as described herein.
Figure 9A:
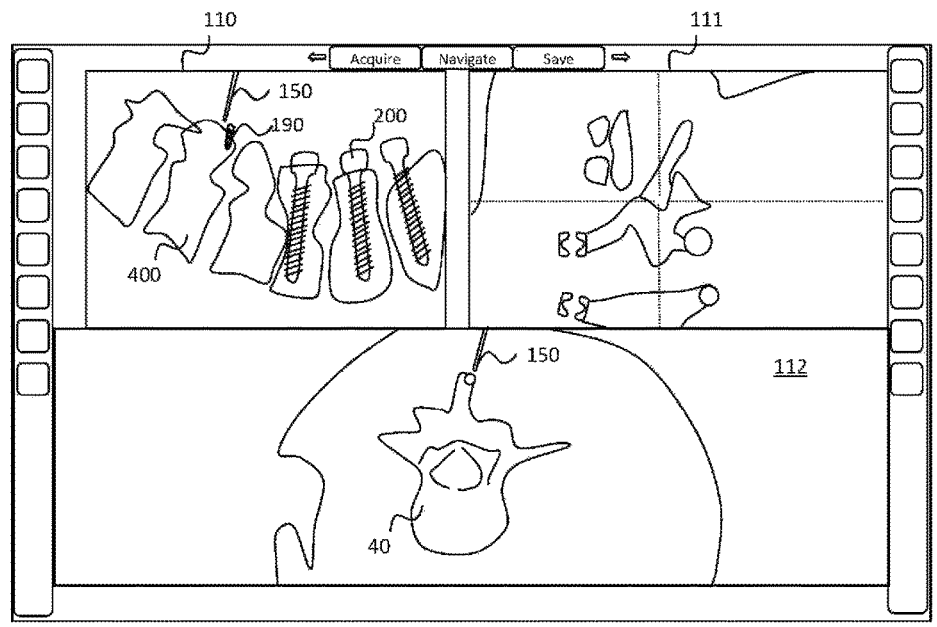
Figure 9B:
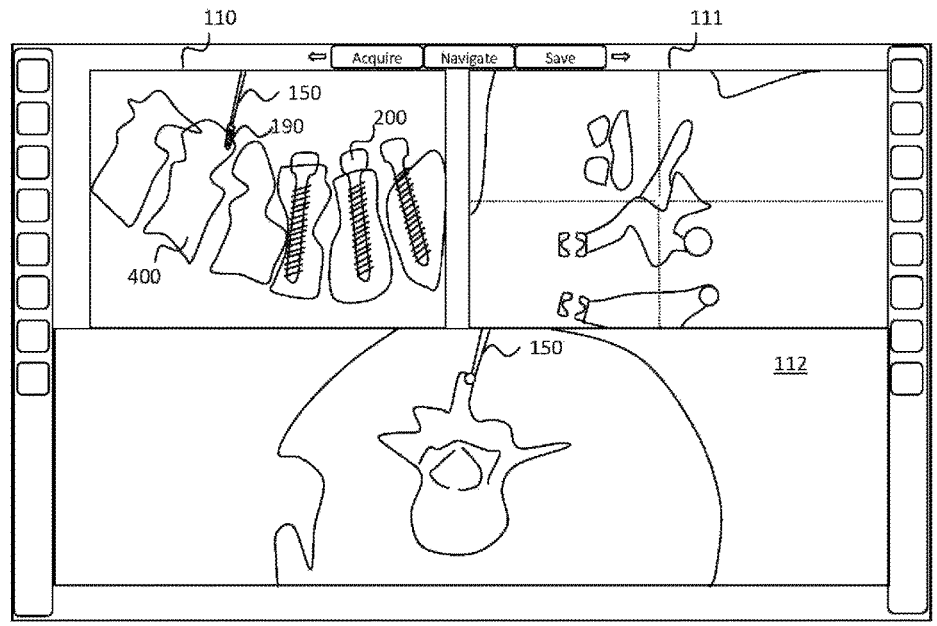
Figure 10:
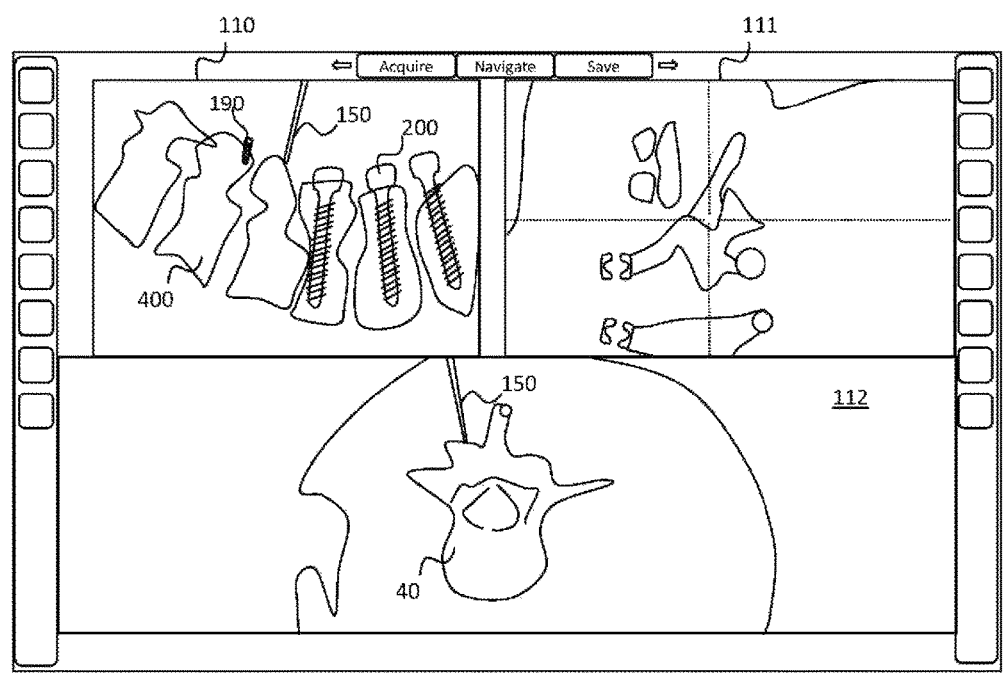

Example illustrations of outputs of the display according to embodiments of the present disclosure are represented in FIGS. 8 to 10. Each display presents three different display regions 110, 111, 112, the display regions 111, 112, 113 each displaying a CT scan taken in a different anatomical plane. In each display region, a scan of the spine 400, pedicle screws 200 and a fiduciary screw 190 is observable. Additionally, a superimposed image of the end of the probe 150 is visible.

As shown in FIG. 8, the probe can be used to find a path down the pedicle of a vertebra in order to place a further pedicle screw. As superimposed on one display region 112, the width of the pedicle has been measured to show it is 5.8 mm wide, aiding in selection of the screw diameter, e.g. a screw of 5.5 mm diameter. This demonstrates why, when, e.g., a 5.5 mm screw is placed down a pedicle 5.8 mm wide, the accuracy of the navigation's registration to the anatomy is of high importance.

As show in FIG. 9a, the superimposed probe 150 is shown almost touching a scanned fiduciary screw 190. This has occurred when the surgeon is touching a real screw 19 with probe 15. This is indicative that correction of the image alignment is needed. Using the system according to the present disclosure, the image alignment can be corrected as shown in FIG. 9b, so that the superimposed probe 150 is shown touching the scanned fiduciary screw 190.

FIG. 10 shows the superimposed probe 150 resting on a plate of the scanned spine 400. Vertebral bone is being removed (decompressed; a laminectomy) to relieve pressure on the dural sac and neural tissue underneath it. The bone is being removed with a burr and it would be an unfavourable result if the burr got confused with the neural tissue. Here the navigation is showing how much bone is left as it is burred away. The procedure, comprises burring a portion of the bone, checking navigation accuracy according to the present disclosure (e.g., using 3 fiduciary screws in the vertebra to achieve 3D image registration or re-registration), burring a further portion of bone, and so on. This shows the value of vertebra-specific accuracy for the navigation.

It will be appreciated by persons skilled in the art that numerous variations and/or modifications may be made to the above-described embodiments, without departing from the broad general scope of the present disclosure. The present embodiments are, therefore to be considered in all respects as illustrative and not restrictive.

The invention claimed is:
1. A system for aiding spinal surgery on a patient comprising:
 a display device;
 a storage device that stores one or more images of at least a portion of the spine of the patient, the one or more images including one or more removable surgical navi- gation markers configured to be mounted to one or more vertebrae of the spine, for display on the display device;

a probe comprising a tip which engages the one or more removable surgical navigation markers; and an analyser comprising a processor and software which causes the processor to receive positional data of the probe based on positioning of the probe relative to said one or more removable surgical navigation markers on the patient, wherein the positional data comprises images of the probe engaged to at least one of the one or more removable surgical navigation markers obtained during a surgical procedure, determine correctional data to adjust an alignment of an image on said display device to match locations of said one or more removable surgical navigation markers in the image based on a comparison of the positional data of the probe and positioning of the one or more removable surgical navigation markers in the image, and cause the display device to adjust positioning of at least part of one or more of the vertebrae in the image displayed on the display device based on the correctional data.

2. The system of claim 1, wherein the one or more removable surgical navigation markers include a first navigation marker mounted to a piece of vertebrae.

3. The system of claim 2, wherein the first navigation marker comprises or supports one or more reflective components, such as reflective balls, which reflect a preselected frequency of light, such as infrared light.

4. The system of claim 1, wherein the one or more removable surgical navigation markers comprise one or more fiduciary screws.

5. The system of claim 1, wherein the one or more removable surgical navigation markers comprise one or more pedicle screws or craniofacial screws.

6. The system of claim 5, wherein the one or more of the pedicle screws comprise a shank, a drive system and a head portion.

7. The system of claim 6, wherein the head portion is polyaxially connected to the shank and during an insertion of the pedicle screw into a spine of the patient, the polyaxial feature is disableable or obviatable.

8. The system according to claim 5, wherein at least one of the pedicle screws is inserted into the body through a tube and the pedicle screw comprises an extension portion that extends at least partially through the tube, wherein extension portion is adapted for contact by the probe to at least partially determine the positional data.

9. The system of claim 1, wherein at least one of the one or more removable surgical navigation markers comprises a connector which engages the probe.

10. The system of claim 9, wherein the connector comprises a cap positioned on a head of the at least one of the one or more removable surgical navigation markers.

11. The system of claim 1, wherein the software causes the processor to: receive positional data from the probe based on positioning of the probe relative to at least one further marker that is not previously represented in the image on the display device and, based on the positional data, add a representation of the at least one further marker to the image displayed on the display device that is indicative of the positioning of the at least one further marker relative to the patient.

12. The system of claim 11, wherein the at least one further marker is a pedicle screw or other fixation device.

13. The system of claim 11, wherein the representation is a 3-dimensional representation.

14. The system of claim 1, wherein at least one of the one or more removable surgical navigation markers comprises a fine adjustment device to allow the at least one of the one or more removable surgical navigation markers to be rotated and/or translated in up to three axes or planes.

15. The system of claim 1, wherein at least one of the one or more removable surgical navigation markers is positioned away from an area to be resected or operated thereon.

16. The system of claim 1, wherein the image is generated by at least one of a computed tomography device, an MRI device or an X-ray device.

17. The system of claim 1, wherein the software causes the processor to make an initial determination of the position of the one or more removable surgical navigation markers to form a three dimensional solid.

18. The system of claim 17, wherein after the probe engages at least one of the one or more removable surgical navigation markers the correctional data from the probe is used to form a corrected three dimensional solid that is used to realign the image.

19. The system of claim 1, wherein the software causes the processor to cause a lordosis correction, kyphosis correction, scoliosis correction or listhesis correction to be sketched or otherwise superimposed onto the image on the display device to indicate a required movement of screws located on the patient, and to identify features of a bony anatomy of the patient including the spinous processes, lamina, pars interarticularis, articular processes, and/or the transverse processes.

20. The system of claim 1, wherein the probe comprises at least one reflective component for identifying the probe in the images obtained during the surgical procedure.

21. A system for aiding spinal surgery on a patient comprising:

a display device;

one or more removable surgical navigation markers configured to be mounted to one or more vertebrae of a spine of the patient;

a probe comprising a tip which engages the one or more removable surgical navigation markers;

a storage device that stores one or more images of at least a portion of the spine of the patient, including the probe and the one or more removable surgical navigation markers, for display on the display device; and an analyser comprising a processor and software which causes the processor to receive positional data of the probe based on positioning of the probe relative to said one or more removable surgical navigation markers on the patient, wherein the positional data comprises images of the probe engaged to at least one of the one or more removable surgical navigation markers obtained during a surgical procedure, determine correctional data to adjust an alignment of an image on said display device to match locations of said one or more removable surgical navigation markers, in the image based on a comparison of the positional data of the probe and positioning of the one or more removable surgical navigation markers in the image, and cause the display device to adjust positioning of at least part of one or more of the vertebrae in the image displayed on the display device based on the correctional data.

22. The system of claim 21, wherein the probe comprises at least one reflective component for identifying the probe in the images obtained during the surgical procedure.

* * * * *

UNITED STATES PATENT AND TRADEMARK OFFICE
CERTIFICATE OF CORRECTION

PATENT NO. : 10,194,993 B2
APPLICATION NO. : 14/903732
DATED : February 5, 2019
INVENTOR(S) : Gregory James Roger et al.

Page 1 of 1

It is certified that error appears in the above-identified patent and that said Letters Patent is hereby corrected as shown below:

On the Title Page

Column 1, Line 1, delete "A.T.F." and insert -- A.T.F --

Column 1, Line 3, delete "New South Wales (AT)" and insert -- New South Wales (AU) --

Signed and Sealed this
Twenty-third Day of April, 2019

Andrei Iancu
*Director of the United States Patent and Trademark Office*